United States Patent [19]

Aoshima et al.

[11] 4,354,044
[45] Oct. 12, 1982

[54] METHOD FOR PREPARING METHACROLEIN

[75] Inventors: Atsushi Aoshima, Yokohama; Ryoichi Mitsui; Hitoshi Nihei, both of Fuji, all of Japan

[73] Assignee: Asahi Kasei Kogyo Kabushiki Kaisha, Osaka, Japan

[21] Appl. No.: 265,136

[22] Filed: May 20, 1981

[30] Foreign Application Priority Data

May 24, 1980 [JP] Japan ................... 55/69435

[51] Int. Cl.$^3$ ............... C07C 45/32; C07C 45/29
[52] U.S. Cl. ................... 568/479; 568/471; 568/475
[58] Field of Search ........... 568/471, 479, 470, 478, 568/474

[56] References Cited

U.S. PATENT DOCUMENTS

| | | | |
|---|---|---|---|
| 3,168,572 | 2/1965 | Vogee et al. | 568/479 |
| 3,660,479 | 5/1972 | Ondrey et al. | 568/479 |
| 3,716,497 | 2/1973 | Courty | 252/470 |
| 4,025,565 | 5/1977 | Oda et al. | 568/479 |
| 4,035,418 | 6/1977 | Okada et al. | 568/479 |
| 4,065,507 | 12/1977 | Hardman et al. | 568/479 |
| 4,258,217 | 5/1981 | Aoshima et al. | 568/474 |

FOREIGN PATENT DOCUMENTS

| | | | |
|---|---|---|---|
| 2735414 | 2/1978 | Fed. Rep. of Germany | 568/479 |
| 425401 | 8/1963 | Japan | 568/479 |
| 1001505 | 10/1961 | United Kingdom | 568/479 |

*Primary Examiner*—Werren B. Lone
*Attorney, Agent, or Firm*—Sprung, Horn, Kramer & Woods

[57] ABSTRACT

A method for preparing methacrolein by oxidizing isobutylene or tertiary butanol with molecular oxygen, characterized by contacting a gaseous mixture of isobutylene or tertiary butanol, air or oxygen and optionally steam and an inert gas with a catalyst having the general combination:

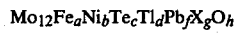

$$Mo_{12}Fe_aNi_bTe_cTl_dPb_fX_gO_h$$

wherein a, b, c, d, f and g represent the numbers of atoms of the respective elements per 12 molybdenum atoms; X is at least one element selected from the group consisting of Cu, Nd and Sm; a is a value of 0.2–6; b is a value of 0.2–6; a+b is a value of 1–10; c is a value of 0.1–4; d is a value of 0.1–3; f is a value of 0.1–5; g is a value of 0.1–5; and h is the number of oxygen atoms for satisfying the valencies of the existing elements. The use of this catalyst enables the selectivity for methacrolein to be improved to 90–94% and the yield based on the starting material to be increased to 89–91%. In addition, the activity of said catalyst is stably maintained for a long period of time.

5 Claims, No Drawings

METHOD FOR PREPARING METHACROLEIN

BACKGROUND OF THE INVENTION

1. Field of the Invention

This invention relates to a process for producing methacrolein in a high yield by oxidizing isobutylene or tertiary butanol with molecular oxygen with a specific catalyst.

2. Description of the Prior Art

Hitherto, many catalysts have been proposed for the gas phase catalytic oxidation of isobutylene or tertiary butanol. From the industrial point of view, however, there are yet many points to be improved.

For example, in the production of methacrolein, the yield of the product, methacrolein, based on the starting material (isobutylene or tertiary butanol) is still so low that the selectivity based on isobutylene is at most about 82–86% even with a catalyst which has hitherto been called an excellent catalyst. Therefore, a catalyst system capable of giving a much higher selectivity is desired. Some of the catalysts containing molybdenum as a main component and additionally containing tellurium exhibit a considerably high yield in the early stage of the reaction. However, their activities drop markedly owing to structual change and scattering of tellurium, and there has been found substantially no catalyst enabling methacrolein to be obtained in a high yield for a long period of time.

When it is intended to produce methacrolein for use as a starting material for the production of a polymer, the methacrolein must be purified. When isobutyraldehyde is contained in the methacrolein as a by-product, the separation of the isobutyraldehyde from the methacrolein to purify the methacrolein is quite difficult because the boiling point of isobutyraldehyde (64.6° C.) is very close to that of methacrolein (73.5° C.). When methyl methacrylate is produced from methacrolein containing a large quantity of isobutyraldehyde, methyl isobutyrate is also formed simultaneously. It is known that if more than 100 ppm of methyl isobutyrate exists in methyl methacrylate, the resulting polymer is opacified or cracked. Therefore, the amount of isobutyraldehyde in the methacrolein used as the starting material for polymerization should be suppressed to 100 ppm or less.

Therefore, a catalyst system capable of suppressing the amount of the by-product, isobutyraldehyde, to 100 ppm or less is desired. When it is intended to use the resulting methacrolein as a starting material for producing an unsaturated ester directly from an unsaturated aldehyde, it is desired that the amount of by-products such as methacrylic acid and acetic acid is as small as possible. Thus, the use as an industrial catalyst involves a number of problems. The present inventors have conducted earnest and detailed studies with the aim of solving the above-mentioned problems. As a result, this invention has been accomplished.

SUMMARY OF THE INVENTION

According to this invention, there is provided a method for preparing methacrolein by oxidizing isobutylene or tertiary butanol with molecular oxygen, characterized by using a catalyst having the general composition:

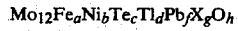

$Mo_{12}Fe_aNi_bTe_cTl_dPb_fX_gO_h$ wherein a, b, c, d, f and g represent the numbers of atoms of the respective elements per 12 molybdenum atoms; X represents at leatt one element selected from the group consisting of Cu, Nd and Sm; a is a value of 0.2–6; b is a value of 0.2–6; a+b is a value of 1–10; c is a value of 0.1–4; d is a value of 0.1–3; f is a value of 0.1–5; g is a value of 0.1–5; and h is the number of oxygen atoms for satisfying the valencies of the existing elements.

The characteristic feature of this invention consists in that, by the use of said catalyst, the selectivity for methacrolein is as high as 90% or more and methacrolein is obtained from isobutylene or tertiary butanol with a high selectivity. Accordingly, the amounts of methacrylic acid, acetic acid, acetone, and the like, which are by-products, are very small. For example, acetic acid is formed in an amount of 0.1 to 1% by weight as a by-product with a conventional catalyst, while the amount of acetic acid formed with the catalyst of this invention is very small such as 0.05 to 0.1%. Accordingly, the process for treating the by-products, such as equippment for treating waste water or the like, can be made compact. Moreover, in spite of the fact that the catalyst of this invention contains tellurium as a promoter, substantially no reduction of catalyst activity is seen, and the high yield of methacrolein can be maintained for a long period of time. Moreover, the catalyst of this invention is characterized in that the amount of isobutyraldehyde, which is very difficult to separate because the difference in boiling point between isobutyraldehyde and methacrolein is only 9° C., formed with said catalyst is very small. Therefore, there is required no separation step accompanied by difficult distillation operation of isobutyraldehyde.

In the catalyst of this invention, molybdenum is an essential component. A system having the catalyst composition from which molybdenum has been excluded has so low an activity that no improvement in yield of methacrolein is expected.

Tellurium is used as a promoter. Tellurium as a promoter has hitherto been used for improving the catalyst activity and selectivity. However, catalysts containing tellurium have hitherto been regarded as impractical because their activity decreases rapidly, even though they are excellent in initial activity and selectivity.

In this invention, in order to remove the above disadvantages, iron, nickel, lead, thallium and the X component are contained together in the catalyst, and iron, nickel and the X component prevent the activity from being reduced, impart a high activity to the catalyst and maintain the high activity for a long period of time.

When any one of iron and nickel is omitted, the effect mentioned above cannot be obtained, and when the total amount of the iron and nickel contained becomes larger than the amount of molybdenum the function of molybdenum as main catalyst is affected, and hence, this is not desirable.

The X component is used in a proportion of 0.1–5 moles, preferably 0.5–3 moles, per 12 moles of molybdenum. When the proportion of the X component is outside the above range, the activity and selectivity are reduced.

The addition of an alkali component and thallium has heretofore been conducted to enhance the selectivity for methacrolein. However, it has been found that only thallium has an effect different from the other components and not only enhances the selectivity but also prevents the reduction of catalyst activity and enables the high activity to be maintained for a long period of time. In addition, said effect of addition of thallium is obtained only when iron, nickel and the X component are present in amounts within the above-mentioned ranges.

The lead component is also very important in the catalyst of this invention, and when it is used in a system comprising iron, nickel and the X component as essential components, a particular effect can be obtained. First of all, it has an effect of remarkably enhancing the activity of the catalyst of this invention, and secondly, it enables the selectivity for methacrolein to be maintained at a very high level. Thirdly, it has the feature that even when the proportion of oxygen to isobutylene is decreased, the selectivity is not reduced. In order to obtain the above-mentioned effects, lead must be used in a proportion of 0.1-5 moles per 12 moles of molybdenum.

As a carrier for the catalyst of this invention, known ones such as silica, silicon carbide, alumina and the like may be used, among which silica sol and silica gel are particularly excellent. The catalyst of this invention can be prepared, for example, in the following manner: Water-soluble compounds of iron, nickel and thallium, a compound of lead, and a water-soluble X component compound are added to an aqueous solution of ammonium molybdate, and an oxide of tellurium is added to the resulting mixture. Furthermore, silica sol is added thereto as a carrier. The mixture is evaporated to dryness on a water bath, preliminarily calcined in the presence of air or oxygen and subsequently subjected to main calcination. Usually, the preliminary calcination is carried out at a temperature of 100°–500° C. and preferably 200°–400° C. The main calcination is usually carried out at a temperature of 400°–1,000° C., preferably 500°–700° C., more preferably 500°–650° C.

As the starting materials of the respective elements used in the preparation of the catalyst of this invention, there may be used not only oxides but also any substances so far as they constitute the catalyst of this invention upon being calcined. Examples of said substances include ammonium salts, inorganic acid salts such as nitrate, carbonate and the like and organic acid salts such as acetate and the like, of the above-mentioned elements. The catalyst may be used either in the form of powder, or in a granular form, or as tablet.

As the reactor, either fixed bed or fluidized bed may be used. The reaction of this invention is carried out at a temperature ranging from 200° to 550° C., preferably from 250° to 450° C. at a pressure of 0.5–10 atmospheres, preferably a pressure ranging from atmospheric pressure to 2 atmospheres.

The contact time between said catalyst and the starting gaseous mixture comprising isobutylene or tertiary butanol, air (or oxygen), steam and an inert gas is 0.1 to 15 seconds, preferably 0.2 to 10 seconds, in the case of atmospheric pressure. The flow rate of the starting gas fed to the catalyst is generally a space velocity of 100 to 5,000 $hr^{-1}$, preferably 200 to 2,000 $hr^{-1}$.

The gaseous mixture comprises 0.5 to 4 moles, preferably 1.4 to 2.5 moles, of oxygen per mole of isobutylene or tertiary butanol. Though steam is not essential, it is advantageous in the aspect of yield to add steam in an amount of 1 to 30 moles, preferably 2 to 15 moles, per mole of isobutylene or tertiary butanol. Moreover, the addition of an inert gas, such as $N_2$, He, Ar, $CO_2$ or the like, may be varied depending upon the variation of the composition of other components.

By using the catalyst of this invention described above in detail, the selectivity for methacrolein reaches even 90–94%. The yield based on the starting material (isobutylene or tertiary butanol) becomes 89–91%. A catalyst capable of giving such a high selectivity and maintaining its activity stably for a long period of time is very epoch-making.

DESCRIPTION OF PREFERRED EMBODIMENTS

This invention is further explained in more detail below referring to Examples, which are merely by way of illustration and not by way limitation.

EXAMPLE 1

In 200 ml of distilled water was dissolved 21.2 g of ammonium paramolybdate, and to the resulting solution were added 2.9 g of nickel nitrate, 0.80 g of thallium nitrate, 2.4 g of copper nitrate and 4.55 g of telluric acid. The resulting solution is hereinafter referred to as "Solution A". On the other hand, 6.6 g of lead nitrate and 4.04 g of iron nitrate were dissolved in 200 ml of distilled water. The resulting solution was mixed with Solution A, and 52.43 g of silica sol (Snowtex N 30) was added thereto. Then, this mixture was evaporated to dryness on a water bath, and the residue was preliminarily calcined in the presence of air at 250° C. for two hours. The calcined product was pulverized to 10–28 meshes and then calcined in the presence of air at 650° C. for 4 hours. The catalyst thus obtained had the following composition:

$Mo_{12}Pb_2Fe_1Ni_1Tl_{0.3}Cu_1Te_2O_h$.

EXAMPLE 2

A Pyrex reaction tube having an inner diameter of 5 mm was packed with 5 g of the catalyst prepared in Example 1, and reaction was carried out therein at a reaction temperature of 360°–440° C. The starting gas had a molar ratio of isobutylene/$O_2$/$H_2O$/He = 3/6/20/71. The contact time was 2.5 seconds. The reaction was continuously practised under the same reaction conditions for a continued 3,000 hours. The analysis was carried out with Shimazu 6APrTF Gas Chromatograph, using Chromosorb 101 and Carbosieve columns. The results are shown in Table 1.

EXAMPLES 3–5

Catalysts having the compositions shown in Table 1 were prepared under the same preparative conditions as in Example 1 and reactions were carried out using said catalysts under the same reaction conditions as in Example 2. The results are shown in Table 1.

COMPARATIVE EXAMPLES 1–3

Catalysts having the compositions shown in Table 1 were prepared under the same preparative conditions as in Example 1, and reaction was carried out using said catalysts under the same reaction conditions as in Example 2. The results are shown in Table 1.

TABLE 1

The change in catalytic activity with lapse of time
(The case of isobutylene)

| No. | Composition of catalyst | Yield of methacrolein (%) | | |
|---|---|---|---|---|
| | | At the start of measurement | After 50 hours | After 3000 hours |
| Example 2 | $Mo_{12}Pb_2Fe_1Ni_1Tl_{0.3}Cu_1Te_2O_h$ | 90.0 | 90.0 | 90.0 |
| Example 3 | $Mo_{12}Pb_2Fe_1Ni_1Tl_{0.3}Sm_1Te_2O_h$ | 89.9 | 89.9 | 89.8 |
| Example 4 | $Mo_{12}Pb_2Fe_1Ni_1Tl_{0.3}Nd_1Te_2O_h$ | 90.1 | 90.1 | 90.1 |
| Example 5 | $Mo_{12}Pb_2Fe_2Ni_2Tl_{0.3}Cu_1Te_2O_h$ | 89.5 | 89.5 | 89.6 |
| Comparative Example 1 | $Mo_{12}Pb_2Fe_1Ni_1Rb_{0.2}Cu_1Te_2O_h$ | 90.1 | 90.1 | 81.0 |
| Comparative Example 2 | $Mo_{12}Pb_2Fe_1Ni_1Cs_{0.2}Cu_1Te_2O_h$ | 89.2 | 89.2 | 80.5 |
| Comparative Example 3 | $Mo_{12}Pb_2Fe_1Ni_1K_{0.2}Cu_1Te_2O_h$ | 88.4 | 88.4 | 78.5 |

EXAMPLES 6–15

A Pyrex reaction tube having an inner diameter of 5 mm was packed with 5 g of each of the catalysts having the compositions shown in Table 2 (the method of preparation was the same as in Example 1), and reactions were carried out therein at a reaction temperature of 360°–440° C. The starting gas had a molar ratio of isobutylene/$O_2$/$H_2O$/He=3/6/20/71. The contact time was 2.5 seconds. The results are shown in Table 2.

COMPARATIVE EXAMPLES 4–11

Using catalysts having the compositions shown in Table 2 (the method of preparation was the same as in Example 1), reactions were carried out under the same reaction conditions as in Examples 6–15. The results are shown in Table 2.

EXAMPLES 16–19

A Pyrex reaction tube having an inner diameter of 5 mm was packed with 5 g of each of the same catalysts as in Examples 2–5, and reactions were carried out therein. The starting gas had a molar ratio of t-butanol/$O_2$/$H_2O$/He=3/6/20/71. The contact time was 2.5 seconds. The reactions were continuously carried out under the same reaction conditions for a period of 3,000 hours. The results are shown in Table 3.

COMPARATIVE EXAMPLES 12–14

Using the same catalyst as used in Comparative Examples 1–3, reaction was carried out under the same reaction conditions as in Examples 16–19. The results are shown in Table 3.

TABLE 2

Activities and selectivities of catalysts
(The case of t-butanol)

| No. | Composition of catalyst | Temperature (°C.) | Conversion of isobutylene (%) | Selectivity for methacrolein (%) |
|---|---|---|---|---|
| Example 6 | $Mo_{12}Fe_4Ni_4Te_2Pb_2Tl_{0.3}Cu_1O_h$ | 400 | 95.8 | 91.6 |
| Example 7 | $Mo_{12}Fe_4Ni_1Te_2Pb_2Tl_{0.3}Cu_1O_h$ | 420 | 94.0 | 93.6 |
| Example 8 | $Mo_{12}Fe_1Ni_4Te_2Pb_2Tl_{0.3}Cu_1O_h$ | 420 | 95.7 | 91.5 |
| Example 9 | $Mo_{12}Fe_1Ni_1Te_2Pb_4Tl_{0.3}Cu_1O_h$ | 400 | 89.5 | 93.2 |
| Example 10 | $Mo_{12}Fe_1Ni_1Te_2Pb_2Tl_{0.3}Cu_4O_h$ | 420 | 96.8 | 90.5 |
| Example 11 | $Mo_{12}Fe_1Ni_1Te_4Pb_2Tl_{0.3}Cu_1O_h$ | 400 | 96.3 | 91.6 |
| Example 12 | $Mo_{12}Fe_1Ni_1Te_2Pb_2Tl_1Cu_1O_h$ | 400 | 96.9 | 91.2 |
| Example 13 | $Mo_{12}Fe_1Ni_{1.5}Te_2Pb_2Tl_{0.3}Cu_1O_h$ | 420 | 94.8 | 92.4 |
| Example 14 | $Mo_{12}Fe_1Ni_1Te_1Pb_2Tl_{0.3}Cu_1O_h$ | 400 | 97.2 | 90.5 |
| Example 15 | $Mo_{12}Fe_1Ni_1Te_2Pb_1Tl_{0.03}Cu_1O_h$ | 400 | 97.8 | 90.2 |
| Comparative Example 4 | $Mo_{12}Fe_1Ni_1Te_2Pb_2Cu_1O_h$ | 400 | 98.5 | 81.5 |
| Comparative Example 5 | $Mo_{12}Fe_1Ni_1Te_2Pb_2Tl_{0.3}Cu_{12}O_h$ | 420 | 30.2 | 82.8 |
| Comparative Example 6 | $Mo_{12}Fe_1Ni_1Te_2Pb_2Na_{0.2}Cu_1O_h$ | 400 | 96.5 | 84.2 |
| Comparative Example 7 | $Mo_{12}Fe_{0.2}Ni_{0.2}Te_2Pb_2Tl_{0.3}Cu_1O_h$ | 420 | 68.9 | 88.5 |
| Comparative Example 8 | $Mo_{12}Fe_1Te_2Pb_2Tl_{0.3}Cu_1O_h$ | 400 | 54.5 | 84.7 |
| Comparative Example 9 | $Mo_{12}Fe_9Ni_4Te_2Pb_2Tl_{0.3}Cu_1O_h$ | 400 | 63.7 | 80.0 |
| Comparative Example 10 | $Mo_{12}Fe_1Ni_1Te_6Pb_2Tl_{0.3}Cu_1O_h$ | 400 | 92.5 | 86.0 |
| Comparative Example 11 | $Mo_{12}Fe_1Ni_1Te_2Pb_7Tl_{0.3}Cu_1O_h$ | 400 | 63.0 | 86.1 |

TABLE 3

The change in catalytic activity with lapse of time
(The case of t-butanol)

| No. | Composition of catalyst | Yield of methacrolein (%) | | |
|---|---|---|---|---|
| | | At the start of measurement | After 50 hours | After 3000 hours |
| Example 16 | $Mo_{12}Fe_1Ni_1Te_2Pb_2Tl_{0.3}Cu_1O_h$ | 89.8 | 90.0 | 90.0 |
| Example 17 | $Mo_{12}Fe_1Ni_1Te_2Pb_2Tl_{0.3}Sm_1O_h$ | 89.9 | 90.0 | 89.9 |
| Example 18 | $Mo_{12}Fe_1Ni_1Te_2Pb_2Tl_{0.3}Nd_1O_h$ | 89.9 | 89.9 | 89.9 |
| Example 19 | $Mo_{12}Fe_2Ni_2Te_2Pb_2Tl_{0.3}Cu_1O_h$ | 89.5 | 89.4 | 89.5 |
| Comparative Example 12 | $Mo_{12}Fe_1Ni_1Te_2Pb_2Rb_{0.2}Cu_1O_h$ | 90.1 | 90.1 | 81.1 |
| Comparative Example 13 | $Mo_{12}Fe_1Ni_1Te_2Pb_2Cs_{0.2}Cu_1O_h$ | 89.1 | 89.1 | 80.4 |
| Comparative Example 14 | $Mo_{12}Fe_1Ni_1Te_2Pb_2K_{0.2}Cu_1O_h$ | 88.3 | 88.3 | 78.4 |

EXAMPLES 20-29

A Pyrex reaction tube having an inner diameter of 5 mm was packed with 5 g of each of the catalysts having the compositions shown in Table 4 (the method of preparation was the same as in Example 1), and reactions were carried out therein at a reaction temperature of 360°–440° C. The starting gas had a molar ratio of 6-butanol/$O_2$/$H_2O$/He = 3/6/20/71. The contact time was 2.5 seconds. The results are shown in Table 4.

TABLE 4

Activities of catalysts and selectivities
(The case of t-butanol)

| No. | Composition of catalyst | Temperature (°C.) | Conversion of isobutylene (%) | Selectivity for methacrolein (%) |
|---|---|---|---|---|
| Example 20 | $Mo_{12}Fe_1Ni_4Te_2Pb_2Tl_{0.3}Cu_1O_h$ | 400 | 95.7 | 91.7 |
| Example 21 | $Mo_{12}Fe_4Ni_1Te_2Pb_2Tl_{0.3}Cu_1O_h$ | 420 | 94.0 | 93.7 |
| Example 22 | $Mo_{12}Fe_4Ni_4Te_2Pb_2Tl_{0.3}Cu_1O_h$ | 420 | 95.6 | 91.5 |
| Example 23 | $Mo_{12}Fe_1Ni_1Te_3Pb_4Tl_{0.3}Cu_1O_h$ | 400 | 89.4 | 93.3 |
| Example 24 | $Mo_{12}Fe_1Ni_1Te_4Pb_2Tl_{0.3}Cu_1O_h$ | 420 | 96.8 | 90.5 |
| Example 25 | $Mo_{12}Fe_1Ni_1Te_2Pb_2Tl_1Cu_1O_h$ | 400 | 96.2 | 91.6 |
| Example 26 | $Mo_{12}Fe_1Ni_{1.5}Te_2Pb_2Tl_{0.3}Cu_1O_h$ | 400 | 96.9 | 91.3 |
| Example 27 | $Mo_{12}Fe_1Ni_1Te_1Pb_2Tl_{0.3}Cu_1O_h$ | 420 | 94.7 | 92.4 |
| Example 28 | $Mo_{12}Fe_1Ni_1Te_2Pb_2Tl_{0.3}Cu_4O_h$ | 400 | 97.2 | 90.5 |
| Example 29 | $Mo_{12}Fe_1Ni_1Te_2Pb_2Tl_{0.1}Cu_1O_h$ | 400 | 97.8 | 90.3 |
| Comparative Example 15 | $Mo_{12}Fe_1Ni_1Te_2Pb_2Cu_1O_h$ | 400 | 98.0 | 81.7 |
| Comparative Example 16 | $Mo_{12}Fe_1Ni_1Te_2Pb_2Tl_{0.3}Cu_{12}O_h$ | 420 | 40.1 | 82.8 |
| Comparative Example 17 | $Mo_{12}Fe_1Ni_1Te_2Pb_2Na_{0.2}Cu_1O_h$ | 400 | 96.4 | 84.2 |
| Comparative Example 18 | $Mo_{12}Fe_{0.2}Ni_{0.2}Te_2Pb_2Tl_{0.3}Cu_1O_h$ | 420 | 68.5 | 88.6 |
| Comparative Example 19 | $Mo_{12}Fe_1Te_2Pb_2Tl_{0.3}Cu_1O_h$ | 400 | 54.6 | 84.5 |
| Comparative Example 20 | $Mo_{12}Fe_9Ni_4Te_2Pb_2Tl_{0.3}Cu_1O_h$ | 400 | 63.6 | 80.0 |
| Comparative Example 21 | $Mo_{12}Fe_1Ni_1Te_6Pb_2Tl_{0.3}Cu_1O_h$ | 400 | 92.0 | 84.3 |
| Comparative Example 22 | $Mo_{12}Fe_1Ni_1Te_2Pb_7Tl_{0.3}Cu_1O_h$ | 400 | 63.0 | 86.2 |

What we claim is:

1. A process for producing methacrolein by oxidizing isobutylene or tertiary butanol with molecular oxygen in the presence of a catalyst, characterized in that said catalyst has the general composition:

$$Mo_{12}Fe_aNi_bTe_cTl_dPb_fX_gO_h$$

wherein
a, b, c, d, f and g represent the number of atoms of the respective elements per 12 molybdenum atoms;
X represents at least one element selected from the group consisting of Cu, Nd and Sm;
a is a value of 0.2–6;
b is a value of 0.2–6;
a+b is a value of 1–10;
c is a value of 0.1–4;
d is a value of 0.1–3;
f is a value of 0.1–5;
g is a value of 0.1–5; and
h is the number of oxygen atoms for satisfying the valencies of the existing elements,
the reaction being carried out at a temperature of 200°–550° C. at a pressure of 0.5–10 atmospheres for 0.1 to 15 seconds at a space velocity of 100 to 5000 hr$^{-1}$.

2. A process according to claim 1, wherein said catalyst is supported on a carrier.

3. A process according to claim 2, wherein said carrier is silica, silicon carbide or alumina.

4. A process according to claim 1, 2 or 3, wherein the reaction is carried out at a temperature of 250°–450° C. at a pressure ranging from atmospheric pressure to 2 atmospheres.

5. A process according to claim 1, 2 or 3, wherein a gaseous mixture comprising isobutylene or tertiary butanol, air or oxygen, steam and an inert gas is contacted with said catalyst under atmospheric pressure.

* * * * *